(12) United States Patent
Kellomaki

(10) Patent No.: US 10,072,219 B2
(45) Date of Patent: *Sep. 11, 2018

(54) METHOD FOR ON-LINE IMAGING OF MESOPHASE PARTICLES

(71) Applicant: Honeywell Limited, Mississauga (CA)

(72) Inventor: Markku Kellomaki, Kuopio (FI)

(73) Assignee: Honeywell Limited, Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/870,864

(22) Filed: Jan. 13, 2018

(65) Prior Publication Data

US 2018/0134973 A1    May 17, 2018

Related U.S. Application Data

(62) Division of application No. 15/226,340, filed on Aug. 2, 2016, now Pat. No. 9,902,911.

(51) Int. Cl.
| | |
|---|---|
| *G01N 21/00* | (2006.01) |
| *C10G 47/36* | (2006.01) |
| *G01N 15/02* | (2006.01) |
| *C10G 47/02* | (2006.01) |
| *G01N 15/06* | (2006.01) |

(52) U.S. Cl.
CPC ............ *C10G 47/36* (2013.01); *C10G 47/02* (2013.01); *G01N 15/0205* (2013.01); *G01N 15/06* (2013.01); *G01N 2015/0693* (2013.01)

(58) Field of Classification Search
CPC ............ G01N 15/0205; G01N 15/06; G01N 2015/0693; C10G 47/02; C10G 47/36
See application file for complete search history.

(56) References Cited

U.S. PATENT DOCUMENTS

2004/0004717 A1 * 1/2004 Reed ................ G01N 15/0211
356/338

* cited by examiner

*Primary Examiner* — Michael P Stafira
(74) *Attorney, Agent, or Firm* — Charles H Jew

(57) ABSTRACT

On-line detection of mesophase particles employs a laser diode light source to illuminate a target area with a pulsed laser linearly or circularly polarized probe beam. Analysis of images determines extent of presence the birefringent mesophase particles, which are precursors to coking in catalytic hydrocracking processes. The inherently polarized low-coherence, unfocused but sufficiently collimated, pulsed laser beam yield sharp imaging with high depth of field of very small mesophase particles that are present in a moving, dark reactor liquid environment.

20 Claims, 4 Drawing Sheets

METHOD FOR ON-LINE IMAGING OF MESOPHASE PARTICLES

REFERENCE TO RELATED APPLICATION

This application is a divisional application of U.S. patent application Ser. No. 15/226,340 which was filed on Aug. 2, 2016, which is incorporated herein by reference.

FIELD OF THE INVENTION

The present invention generally relates to sensors and methods for detecting the presence of mesophase particles, which are precursors of coking, and more particularly to techniques of using an inherently polarized, unfocused but sufficiently collimated, pulsed laser beam illumination for on-line linear-polarized light imaging and circular-polarized light imaging of the mesophase particles.

BACKGROUND OF THE INVENTION

In heavy oil upgrading, heavier materials are converted to lighter fractions and most of the sulfur, nitrogen and metals must be removed. Heavy oils include materials such as petroleum crude oil, atmospheric tower bottoms products, vacuum tower bottoms products, heavy cycle oils, shale oils, coal derived liquids, crude oil residuum, topped crude oils and the heavy bituminous oils extracted from oil sands. Most residual oil feedstocks which are to be upgraded contain some level of asphaltenes which are typically understood to be heptane insoluble compounds. Asphaltenes are high molecular weight compounds containing heteroatoms which impart polarity.

Heavy oil is upgraded in a primary upgrading unit before it can be further processed into useable products. Primary upgrading units known in the art include coking processes, such as delayed or fluidized coking, and hydrogen addition processes such as ebullated bed or slurry hydrocracking (SHC). In SHC, a three-phase mixture of heavy liquid oil feed cracks in the presence of gaseous hydrogen over solid catalyst to produce lighter products under pressure at an elevated temperature. During an SHC reaction, it is important to minimize coking. Under certain process conditions, the asphaltenes can self-associate, or flocculate to form larger molecules, generate a mesophase and precipitate out of solution to form coke. Mesophase is a semi-crystalline carbonaceous material defined as round, anisotropic particles. The presence of mesophase can serve as a warning that operating conditions are too severe in the SHC reactor and that coke formation is likely to occur under prevailing condition.

The formation of mesophase particles is typically monitored by labor-intensive laboratory analysis that entail several hours of delay to actual process events. Industry is in need of a fast, on-line method of monitoring the volume fraction and size distribution of mesophase particles.

SUMMARY OF THE INVENTION

The present invention is based in part on the recognition that obtaining sharp imaging with high depth of field of very small mesophase particles that are present in a moving, dark (high light absorption) reactor liquid environment can be achieved by using illumination from an inherently polarized, low-coherence, unfocused but sufficiently collimated, pulsed laser beam.

Mesophase particles in many chemical processes are precursors before coking. They are anisotropic liquid crystal particles which consist of layered structures of polyaromatics. These particles behave like an emulsion: particles can grow, coalesce and develop into coke in reactors. The structures of mesophase particles make them visible using cross-polarized light microscopy. Mesophase particles are birefrigent so they turn incident linearly polarized light into elliptically polarized light which can be observed in reflection or transmission behind a linear polarizer mounted 90 degrees with respect to the incident polarization direction. Only changed polarization states will be observed.

The on-line cross-polarized light imaging technique enables precise measurements of mesophase particle volume fraction and particle size distribution in the reactor liquid. The pulsed laser beam can be directly used for linear-polarized light imaging or for circular-polarized light imaging preferably with the use of quarter-wave plates.

In one aspect, the invention is directed to an on-line method for detection of mesophase particles formed in a hydrocarbon conversion reactor that includes the steps of:

(a) establishing a continuous reactor fluid stream containing mesophase particles;

(b) employing a laser diode light source to illuminate a target area of the reactor fluid stream with a pulsed laser probe beam along a first beam path that comprises linearly polarized light or circularly polarized light such that an output beam emerges (either reflected or transmitted) from the target area along a second beam path;

(c) obtaining an image of the mesophase particles in the continuous reactor fluid stream; and (d) analyzing the image to determine at least one of (i) volume fraction or (ii) size distribution of mesophase particles in the continuous reactor fluid stream.

In another aspect, the invention is directed to a method of converting a heavy hydrocarbon feed into light hydrocarbon products that includes the steps of:

(a) mixing a heavy hydrocarbons liquid feed with catalyst particles to form a slurry;

(b) hydrocracking heavy hydrocarbons in the slurry in the presence of hydrogen in a reactor to produce a hydrocracked slurry product comprising lighter hydrocarbon products wherein the slurry product is withdrawn from the reactor;

(c) monitoring mesophase particles in the reactor by (i) directing a pulsed laser probe beam from a laser diode light source along a first beam path into a continuous reactor fluid stream wherein the probe beam comprises linearly polarized light or circularly polarized light such that an output beam emerges from the continuous reactor fluid stream along a second beam path, (ii) obtaining an image of the mesophase particles in the continuous reactor fluid stream, and (iii) analyzing the image to determine at least one of volume fraction or size distribution of mesophase particles in the continuous reactor fluid stream; and (d) adjusting reactor conditions to reduce levels of mesophase particles formed during hydrocracking.

In yet another aspect, the invention is directed to a system for in-situ monitoring of mesophase particles formed in a hydrocarbon conversion reactor which generates a reactor fluid that includes:

a laser diode light source that directs a pulsed laser probe beam comprising linearly polarized light or circularly polarized light along a first beam path into the reactor fluid such that an output beam emerges from the reactor fluid along a second beam path;

a polarizing filter positioned in the second beam path that filters the output beam;

a camera that detects the second beam path after passing the polarizing filter and generates signals that represent images of the mesophase particles in the reactor fluid; and means for analyzing the signals to determine at least one of volume fraction or size distribution of mesophase particles in the reactor fluid.

An inherently polarized illumination comprises a linearly polarized radiation with known polarization direction and sufficient polarization level, which is preferably more than 90%. Depending on their configuration, laser sources can produce laser radiation that is randomly polarized or not randomly polarized. In a preferred embodiment as described herein, the laser source used is a linearly polarized laser. Image acquisition using a low coherence laser light source avoids the speckle phenomenon when imaging mesophase particles. Speckle can lead to significant amounts of bright spots on the image which makes it difficult to detect mesophase particles which also appear bright. An unfocused laser source generates light that is not focused on a single spot and which is advantageous for illuminating an area for area-scan imaging. In addition, employing a sufficiently collimated laser beam is important for maintaining adequate illumination intensity which is not overly dependent on the target distance. For example, while it feasible to attain a sufficiently wide but still very collimated beam from a sharply focused single-emitter laser using lens optics, it would be very difficult to avoid speckle using such an arrangement. With the present invention, using a laser illuminator in which a wider beam is constructed by combining multiple diode emitters is able to overcome coherence artifacts.

A laser illuminator can be configured to achieve the desired level of low-coherence by through angle diversity by (i) employing a large number of emitters which diversifies the laser path lengths and angles and/or (ii) using a diffuser which randomizes the spatial angle of distribution that is accompanied by a slight decollimation of the illumination. Another technique to insure low-coherence laser illumination is through wavelength diversity which is also achieved by using a large number of emitters. Each unique emitter, which comprises an individual laser bar, generates radiation with a wavelength that is slightly different. The reason is that the laser bars are not completely identical due to the nature of the manufacturing process.

With the present invention, an "unfocused" laser beam is not employed to illuminate the smallest possible spot in the fluid. For the lens and imaging geometry employed, the laser beam should be sufficiently collimated so that the size of the beam is not excessively large in comparison to the target area. Preferably the laser beam diameter should be less than twice the target area image diameter. If the laser beam diameter is too large, laser energy is wasted and the illumination intensity is not adequate which result in less than optimum motion freezing or the depth of field (DOF) becomes too low. Using a high-power pulsed illumination allows for a smaller lens aperture, which leads to a higher DOF. The laser beam however should be large enough so as to avoid edge effects (vignetting) and be tolerant of relative vibration of the camera and illuminator.

By employing proper laser pulse durations and camera pixel resolution, motion of mesophase particles in a reactor flow channel can be "frozen" with the inventive cross-polarizer imaging techniques. A high DOF renders measurements less sensitive to vibrations and permits a deeper test channel to be used. A thicker portion of the reactor liquid being in focus near to sight window leads to the higher probability of detecting mesophase particles.

DETAILED DESCRIPTION OF PREFERRED EMBODIMENTS

Figure 1:
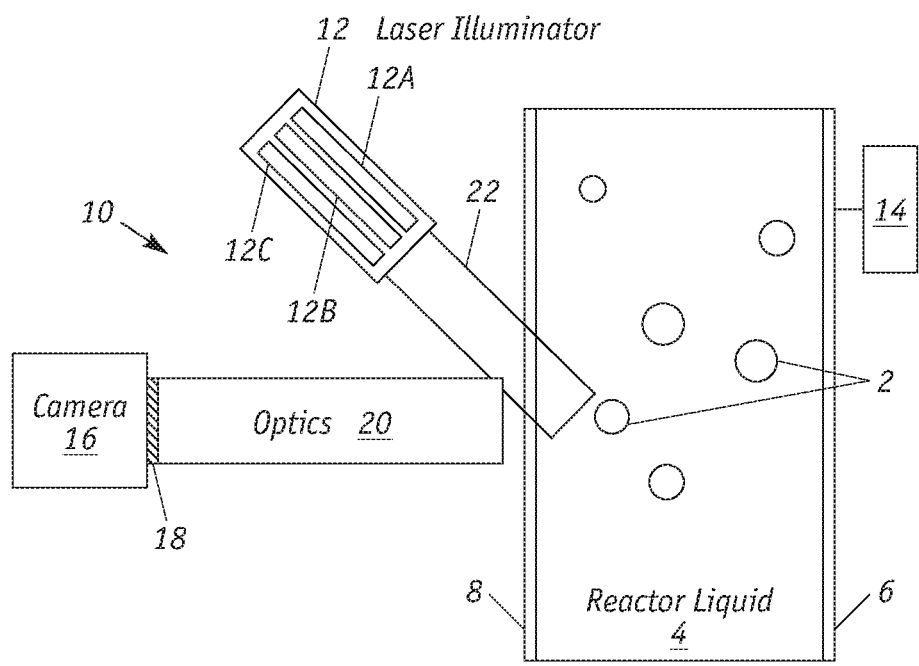
FIG. 1 shows an on-line system for linear-polarized light imaging using obliquely (directional) reflected illumination imaging.

FIG. 1 illustrates a linear-polarized light imaging system 10 for in-situ monitoring of mesophase particles 2 that are present in a moving reactor liquid that is flowing through channel 4 which is defined by window 8 and channel wall 6. The window and channel wall can be a part of side-stream from a reactor chamber with known cross sectional dimensions at the area where the laser beam illuminates a target area in the reactor liquid. The flow rate through the side-stream can be measured by sensor 14. Thus the volumetric flow rate through the channel can be calculated. Window 8 is made of material such as glass or sapphire which is transparent to the laser light.

For linear-polarized light imaging, a laser illuminator 12 directs a laser probe beam 22 through window 8 and into channel 4. A preferred laser illuminator 12 combines the output of a plurality of laser bars 12A, 12B, 12C, by spatial multiplexing to become substantially parallel with an optical axis, while individually rotating the polarization of each diode output so that the combined output has substantially a single (linear) polarization. Each laser bar comprises one or more diode lasers. An exemplary laser illuminator configured with a plurality of laser bars is described in U.S. Pat. No. 7,817,693 to Alahautala et al, which is incorporated herein by reference. A suitable laser illuminator is commercially available as the Cavilux Smart model from Cavitar Oy (Valkeakoski, FI).

The pulsed laser beam 22 preferably has pulse duration of about 10 ns to 10 μs. The required pulse duration depends on image resolution of the imaging device (camera) 16 used and the mesophase velocity of the reactor fluid in channel 4 that is adjacent widow 8. For example, if one pixel movement of the reactor liquid or fluid is permitted for the camera, which results in acceptable blur, the pulse direction $\Delta T < L_P/|V_M|$ where $L_P$ is the pixel size in μm and $V_M$ is the mesophase velocity near the window in μm/μs. The mesophase velocity has two components: $V_M = V_L + V_V$ where $V_L$ is the reactor fluid in the channel and $V_V$ is the relative vibration velocity between the imaging device (camera) and the channel. The mesophase movement is a combination of flow velocity and vibration of the channel. In this example, the laser beam pulse duration is most preferably short enough to allow movement of mesophase particles for up to one pixel during exposure.

Since the laser probe beam 22 that is emitted from laser illuminator 12 is substantially linearly polarized no polarization filter is required on the illumination side however a "clean up" polarization filter can be positioned in front of the laser source if desired to generate a probe beam that is essentially completely linearly polarized. Even without a "clean up" polarization filter, the laser probe beam 22 from laser diodes source will typically be over 90% linearly polarized. The presence of a polarization filter only slightly reduces the intensity as the source is already substantially polarized.

Output light that is backscattered or reflected from mesophase particles 2 is collected by imaging optics 20 and a polarizing filter 18 filters or blocks the component of this backscattered light which has a polarization state parallel to that of the incident laser probe beam 22. Preferably, the unfocused probe beam illuminates a target area in the reactor liquid that typically ranges from about 20 to 25 sq. mm. The size of the illuminated target area is sufficient to permit rapid and accurate detection of the mesophase particles. For a circular target area, the diameter is about 5 mm or for square target area, each side is about 5 mm.

The imaging device or camera 16 images only the component with the polarization state perpendicular to that of laser probe beam 22. Some of the particles that reflect light may not be mesophase particles and some may only be partially mesophasic. Since the dimensions of channel 4 are known and the flow rate through the channel can be measured, the volume fraction of mesophase particles flowing through channel 4 can be calculated by determining the size of the mesophase particles that are detected. The size distribution of mesophase particles flowing through channel 4 can be determined by comparing the images to calibration data measured with mesophase particles of known sizes.

The imaging device 16 and laser illuminator 12 are configured so that the image scale is sufficient to allow individual mesophase particles in the reactor liquid to be discerned. Thus, the imaging detectors, e.g., cameras, should have pixel sizes that do not exceed one quarter of the typical width of mesophase particles. This corresponds to about 0.1 to 5.0 microns per pixel in the imaging detector when using adequate lenses. Conventional lens can be employed as the imaging optics 20 with the camera when the reactor liquid and mesophase particles are moving in a relatively constant rate. However, if reactor liquid flow pattern is turbulent, telecentric lens systems that create large depth of field can be used so that fluctuations in the movements in the reactor liquid relative to the camera does not change image size.

The short exposure time created by the pulsed laser probe beam 22, allows the imaging device 16, with correspondingly short integration times, to obtain good images of the target area in the reactor liquid by reducing or eliminating the adverse effects caused by motion-blurring in the direction of movement of the reactor liquid. In the case of a charge-coupled device (CCD), a short integration time enables pixels to collect less light and a longer integration time enables pixels to collect more light. The higher illumination intensity provided by a laser illuminator is advantageous as more light means a higher signal to noise ratio. CMOS array cameras can also be employed.

Figure 2:
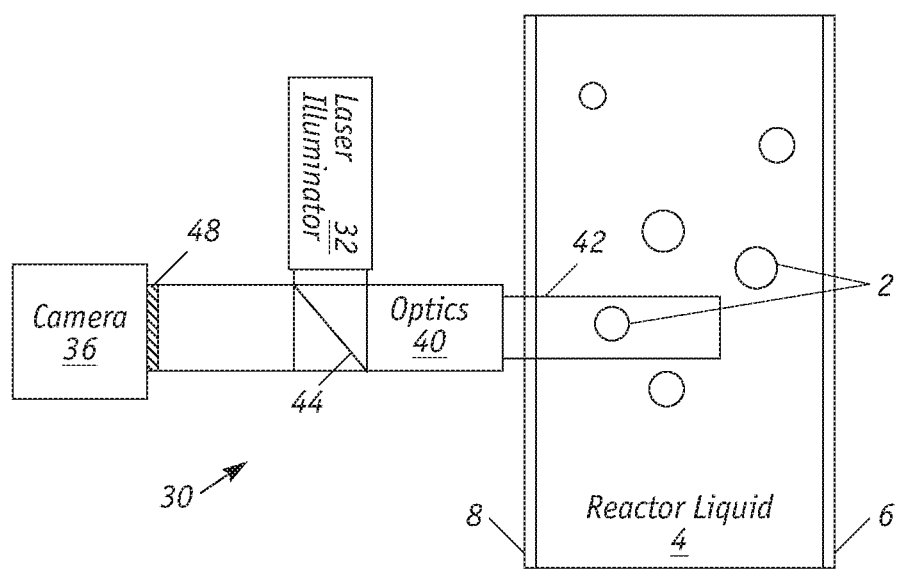
FIG. 2 shows an on-line system for linear-polarized light imaging using reflected illumination imaging (coaxial)

FIG. 2 illustrates a coaxial linear-polarizing light imaging system 30 for in-situ monitoring of mesophase particles 2 that are present in a moving reactor liquid that is flowing through channel 4 which is defined by window 8 and channel wall 6. The laser illuminator 32 generates a pulsed laser probe beam 42 which is directed by beam splitter 44 through window 8 and into channel 4. A preferred laser illuminator 32 has the same configuration as illuminator 12 of FIG. 1. No polarization filter is required on the illumination side but a "clean up" polarization filter can be positioned in front of the laser source if desired.

Output light that is backscattered or reflected from mesophase particles 2 is collected by imaging optics 40 and polarizing filter 48 filters or blocks the component of this backscattered light which has a polarization state parallel to that of the incident laser beam 42. The camera 36 images only the component with the polarization state perpendicular to that of laser probe beam 22.

Figure 3:
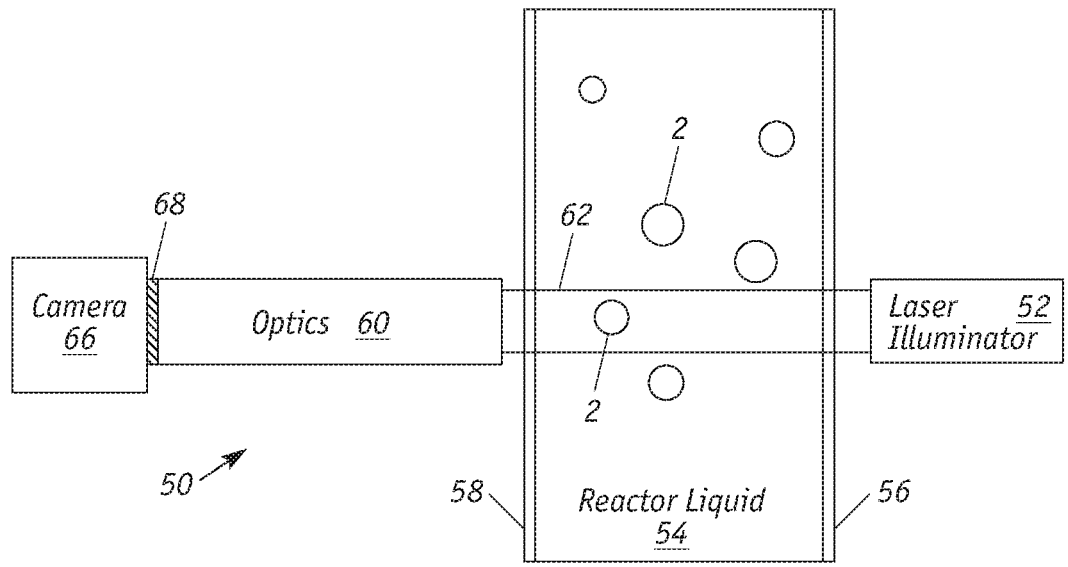
FIG. 3 shows an on-line system for linear-polarized light imaging using transillumination.

FIG. 3 illustrates a linear-polarizing light imaging system 50 for in-situ monitoring of mesophase particles 2 that are present in a moving reactor liquid that is flowing through channel 54 which is defined by windows 56, 58. The windows can be a part of a side-stream from a reactor chamber with known cross sectional dimensions at the area where the laser beam illuminates a target area in the reactor liquid. A laser illuminator 52 directs a pulsed laser probe beam 62 through window 56 and into channel 54. A preferred laser illuminator 52 has the same configuration as illuminator 12 of FIG. 1. No polarization filter is required on the illumination side but a "clean up" polarization filter can be positioned in front of the laser source if desired.

Output light that interacts with mesophase particles 2 is collected by imaging optics 60 and polarizing filter 68 filters or blocks the component of this backscattered light which has a polarization state parallel to that of the incident laser beam 62. The camera 66 images only the component with the polarization state perpendicular to that of beam 62.

Figure 4:
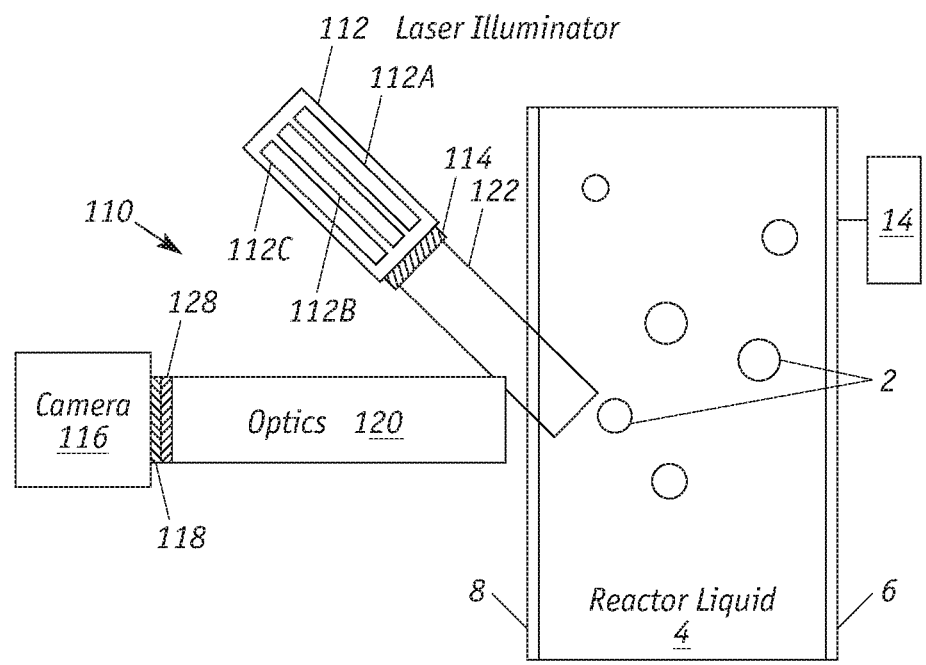
FIG. 4 shows an on-line system for circular-polarized light imaging using obliquely (directional) reflected illumination imaging.
Figure 5:
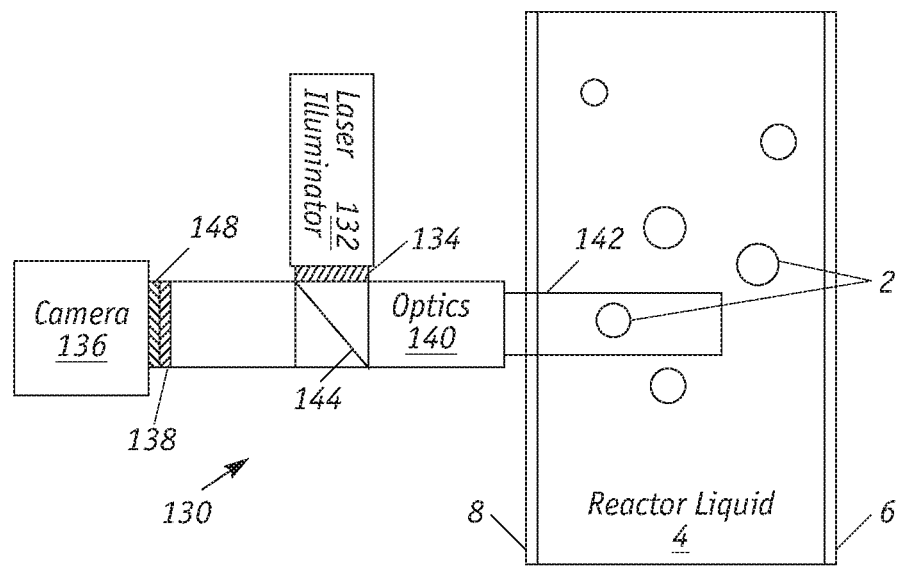
FIG. 5 shows an on-line system for circular-polarized light imaging using reflected illumination imaging (coaxial)
Figure 6:
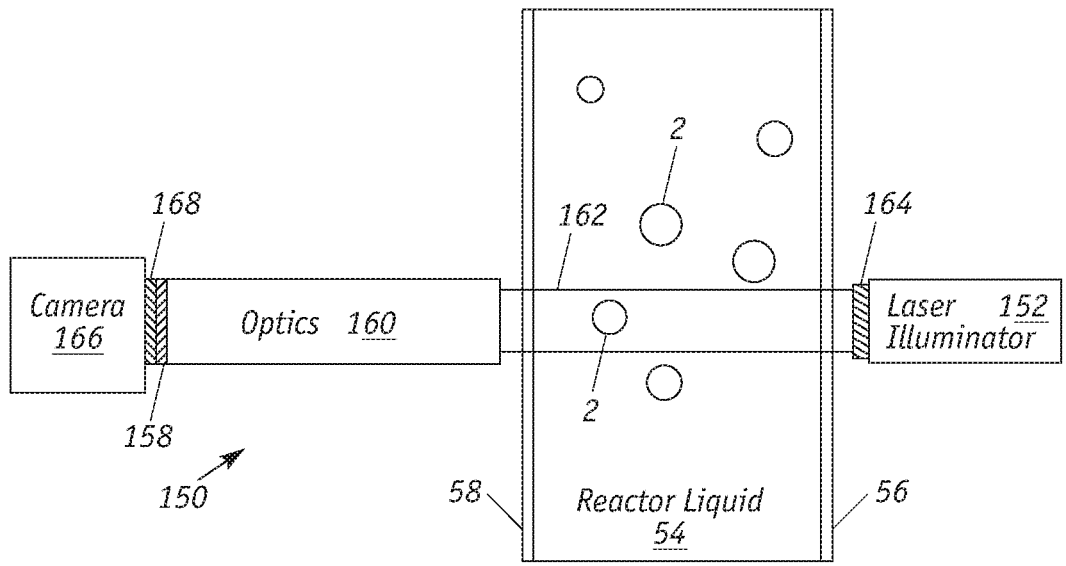
FIG. 6 shows an on-line system for circular-polarized light imaging using transillumination.

With the present invention, circularly polarized light can also be employed to detect the presence of mesophase particles as shown in the on-line systems depicted in FIGS. 4-6. In particular, linearly polarized light is converted into circularly polarized light with a quarter-wave plate. The circularly polarized light interacts with the birefringent mesophase particles and the transmitted or reflected light is analyzed.

FIG. 4 illustrates a circular-polarizing light imaging system 110 for in-situ monitoring of mesophase particles 2 that are present in a moving reactor liquid that is flowing through channel 4 which is defined by window 8 and channel wall 6. A circular polarizing system has the advantage that any angular dependent extinction patterns will be absent. Extinction patterns may introduce dark separating lines into the images of mesophase particles which may make larger particles look like a collection of smaller particles. This will bias the particle size distribution. The window and channel wall can be a part of side-stream from a reactor chamber with known cross sectional dimensions at the area where the laser beam illuminates a target area in the reactor liquid. The flow rate through the side-stream can be measured by a flow sensor 14. Thus the volumetric flow rate through the channel can be calculated. Window 8 is made of material such as glass or sapphire which is transparent to the laser light.

The laser beam that is initially emitted from laser illuminator 112 is substantially linearly polarized. A conventional quarter-wave plate 114, with suitable handedness and orientation, is positioned in front of laser illuminator 112 to convert this initial laser beam of linear polarized light into a circularly polarized light probe beam 122. Even with this quarter-wave plate 114, it is expected that the intensity of laser probe beam 122 will not be attenuated virtually at all with respect to the initial laser beam if the quart-wave plate 114 is oriented correctly.

Laser probe beam 122 passes through window 8 and into channel 4. A preferred laser illuminator 112 multiplexes the output of a plurality of laser bars 112A, 112B, 112C, by spatial multiplexing to become substantially parallel with an optical axis, while individually rotating the polarization of each diode output so that the combined output has substantially a single (linear) polarization. Each laser bar comprises one or more diode lasers. An exemplary laser illuminator configured with a plurality of laser bars is described in U.S. Pat. No. 7,817,693 to Alahautala et al, which is incorporated herein by reference. A suitable laser illuminator is commercially available as the Cavilux Smart model from Cavitar Oy (Valkeakoski, FI).

Output light that is backscattered or reflected from mesophase particles 2 is collected by imaging optics 120. A quarter-wave plate 128, which is configured with suitable handedness and orientation, and a linear polarizing filter 118, which is configured perpendicular to the initial laser beam polarization, filter or block the component of this backscattered light which has a polarization state parallel to that of the incident laser probe beam 122. Preferably, the linear polarizer is first adjusted to be perpendicular with respect to the linearly polarized beam (extinction). Then quarter-wave plates are positioned in front of the illuminator and on top of linear polarizer on the camera side. The camera side quarter-wave plate is adjusted to orientation which leads to extinction. Anisotropic materials like mesophase particles will remain bright in this setup.

Preferably, the unfocused probe beam illuminates a target area in the reactor liquid that typically ranges from 20 to 25 sq. mm. With circular polarization, only light that is scattered from the anisotropic mesophase particles will have suitable polarization state to be visible and their images captured by imaging device or camera 116. Some of the particles that reflect light may not be mesophase particles and some may only be partially mesophasic. The volume fraction and size distribution of mesophase particles flowing through channel 4 can be determined by analyzing the images.

The imaging device 116 and laser illuminator 112 are configured so that the image scale is sufficient to allow individual mesophase particles in the reactor liquid to be discerned. Thus, the imaging detectors, e.g., cameras, should have pixel sizes that do not exceed one quarter of the typical width of mesophase particles. This corresponds to about 0.1 to 5.0 microns per pixel in the imaging detector when using adequate lenses. Conventional lens can be employed as the imaging optics 120 with the camera when the reactor liquid and mesophase particles are moving in a relatively constant rate. However, if reactor liquid flow pattern is turbulent, telecentric lens systems that create large depth of field can be used so that fluctuations in the movements in the reactor liquid relative to the camera does not change image size. The short exposure time created by the pulsed laser probe beam 122, allows the imaging device 116, with correspondingly a short integrations time, to obtain good images of the target area in the reactor liquid by reducing or eliminating the adverse effects caused by motion-blurring in the direction of movement of the reactor liquid. In the case of a charge-coupled device (CCD), a short integration time enables pixels to collect less light and a longer integration time enables pixels to collect more light. The higher illumination intensity provided by a laser illuminator is advantageous as more light means a higher signal to noise ratio. CMOS array cameras can also be employed.

FIG. 5 illustrates a coaxial circular-polarizing light imaging system 130 for in-situ monitoring of mesophase particles 2 that are present in a moving reactor liquid that is flowing through channel 4 which is defined by window 8 and channel wall 6. A laser illuminator 132 generates an initial pulsed laser beam and a quarter-wave plate 134, which is positioned in front of laser illuminator, converts this linearly polarized light into circularly polarized light probe beam 142 which is directed by beam splitter 144 through window 8 and into channel 4. A preferred laser illuminator 132 has the same configuration as illuminator 12 of FIG. 1.

Output light that is backscattered or reflected from mesophase particles 2 is collected by imaging optics 140 and is filtered by a quarter-wave plate 138, which configured with suitable handedness and orientation, and a linear polarizing filter 148, which is configured perpendicular to the initial laser beam polarization. The camera 136 images only the component with the polarization state perpendicular to that of laser probe beam 142, which is characteristic of light scattered from anisotropic particles like mesophase.

FIG. 6 illustrates a circular-polarizing light imaging system 150 for in-situ monitoring of mesophase particles 2 that are present in a moving reactor liquid that is flowing through channel 54 which is defined by windows 56, 58. The windows can be a part of a side-stream from a reactor chamber with known cross sectional dimensions at the area where the laser beam illuminates a target area in the reactor liquid. A laser illuminator 152 directs a pulsed laser probe beam 162 through window 56 and into channel 54. A quarter-wave plate 164 is positioned in front of laser illuminator in order to convert linear polarized light into circularly polarized light. A preferred laser illuminator 152 has the same configuration as illuminator 12 of FIG. 1. No polarization filter is required on the illumination side but a "clean up" polarization filter can be positioned in front of the laser source if desired.

Output light that interacts with mesophase particles 2 is collected by imaging optics 160 and is filtered by a quarter-wave plate 158, which configured with suitable handedness and orientation, and a linear polarizing filter 168, which is configured perpendicular to the initial laser beam polarization. The camera 166 images only the component with the polarization state perpendicular to that of beam 162.

Figure 7:
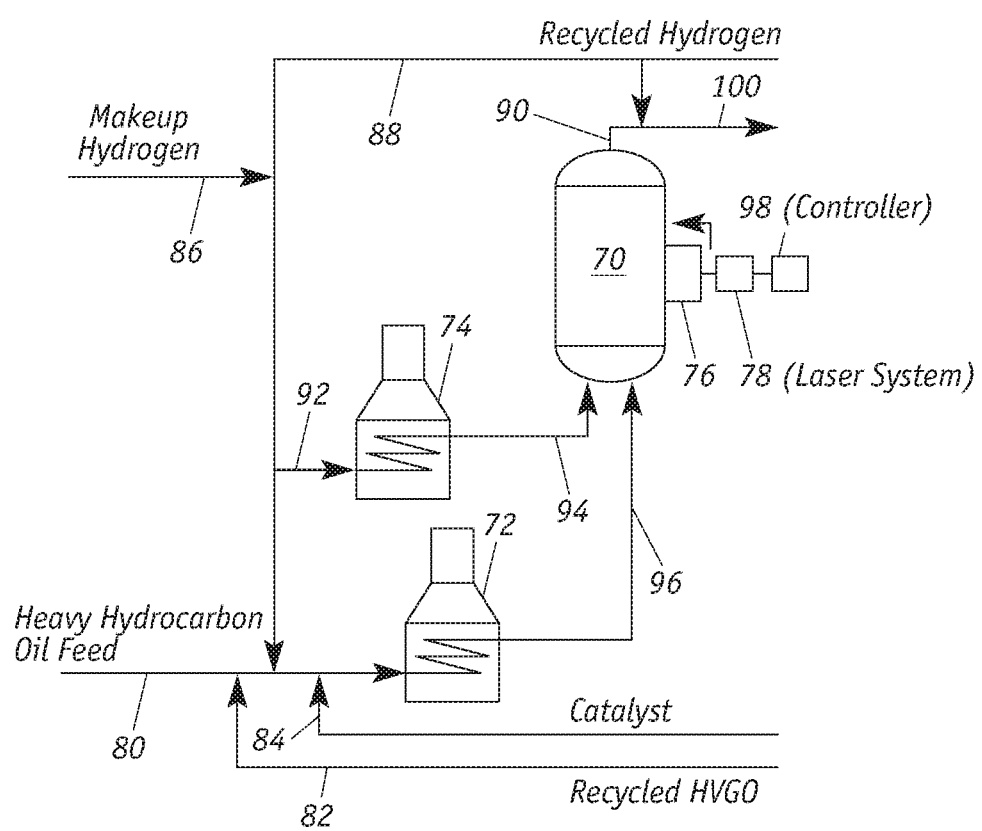
FIG. 7 is a flow diagram of a catalytic slurry hydrocracking process being monitored for mesophase particles.

The on-line imaging techniques of the present invention are particularly suited for monitoring continuous chemical processes to prevent or at least reduce the level of coking. FIG. 7 is shows a catalytic slurry hydrocracking (SHC) process that employs an SHC reactor 70 and heaters 72 and 74. Heavy hydrocarbon oil feed 80 is mixed with hydrogen from makeup hydrogen source 86 and recycled hydrogen source 88, recycled heavy vacuum gas oil (HVGO) 82, and catalyst particles 84 to form a combined feed 96 that is heated in heater 72 and introduced into SHC reactor 70. In addition, secondary source of hydrogen through line 92 is heated in heater 74 and introduced through line 94 into SHC reactor 70, which can be a tubular reactor through which the combined feed, catalyst and gas move upwardly.

A gas-liquid mixture 90 is withdrawn from the top of SHC reactor 70 and mixed with recycled hydrogen to form a combined petroleum stream 100 that undergoes further processing to yield naphtha, diesel and light vacuum gas oil. SHC processing is further described in U.S. Pat. No. 8,123,933 to Bhattacharyya et al., which is incorporated herein by reference. A side-stream 76 diverts a portion of the reactor slurry from a lower portion of SHC reactor 70 to an upper portion of the reactor. An on-line laser system 78 monitors the level of mesophase formation in side-stream 76. A controller 98 that is connected to laser system 78 analyzes digital images from laser system 78 to calculate the volume fraction and/or size distribution of mesophase particles in the reactor. Based on these calculations, the controller 98 adjusts the operating parameters of the SHC process to lower the level of mesophase particles in order to avoid or reduce coking. For example, the temperature, partial pressure of hydrogen, catalyst concentration, SHC reactor flow rate and other parameters can be adjusted. The laser imaging system of the present invention can be applied to any processing stream containing mesophase particles. For example, the bottom streams of further processing units such as a hot high-pressure separator, a hot low-pressure separator etc. can be monitored for mesophase particles. Preferably, the imaging system is installed at a location in the process where bottom stream mesophase content changes reflect changes in the SHC reactor.

A method of controlling the operating parameters of the catalytic SHC process is to develop a mathematical model that simulates the formation of mesophase particles in SHC reactor 70. For instance, the model can predict the onset of mesophase formation and the level of coking based on the temperature, partial pressure of hydrogen, catalyst concentration, SHC reactor flow rate, and other variables. The controller 98 can employ the model to adjust one or more parameters to lower delay or eliminate mesophase formation based on measurements by the laser system 78.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A method of converting a heavy hydrocarbon feed into light hydrocarbon products comprising the steps of:
    (a) mixing a heavy hydrocarbons liquid feed with catalyst particles to form a slurry;
    (b) hydrocracking heavy hydrocarbons in the slurry in the presence of hydrogen in a reactor to produce a hydrocracked slurry product comprising lighter hydrocarbon products wherein the slurry product is withdrawn from the reactor;
    (c) monitoring mesophase particles in the reactor by (i) directing a pulsed laser probe beam from a laser diode light source along a first beam path into a continuous reactor fluid stream wherein the probe beam comprises linearly polarized light such that an output beam emerges from the continuous reactor fluid stream along a second beam path, (ii) obtaining an image of the mesophase particles in the continuous reactor fluid stream, and (iii) analyzing the image to determine at least one of volume fraction or size distribution of mesophase particles in the continuous reactor fluid stream; and
    (d) adjusting reactor conditions to reduce levels of mesophae particles formed during hydrocracking.

2. The method of claim 1 wherein the laser diode light source generates a pulsed laser probe beam without employing a polarizer filter.

3. A method of converting a heavy hydrocarbon feed into light hydrocarbon products comprising the steps of:
    (a) mixing a heavy hydrocarbons liquid feed with catalyst particles to form a slurry;
    (b) hydrocracking heavy hydrocarbons in the slurry in the presence of hydrogen in a reactor to produce a hydrocracked slurry product comprising lighter hydrocarbon products wherein the slurry product is withdrawn from the reactor;
    (c) monitoring mesophase particles in the reactor by (i) directing a pulsed laser probe beam from a laser diode light source along a first beam path into a continuous reactor fluid stream wherein the probe beam comprises circularly polarized light and a quarter-wave plate converts linearly polarized light from the laser diode light source into circularly polarized light such that an output beam emerges from the continuous reactor fluid stream along a second beam path, (ii) obtaining an image of the mesophase particles in the continuous reactor fluid stream, and (iii) analyzing the image to determine at least one of volume fraction or size distribution of mesophase particles in the continuous reactor fluid stream; and
    (d) adjusting reactor conditions to reduce levels of mesophae particles formed during hydrocracking.

4. The method of claim 1 wherein the probe beam is reflected from a target area in the reactor fluid stream to form the output beam.

5. The method of claim 1 wherein the probe beam is transmitted through a target area in the reactor fluid stream to form the output beam.

6. The method of claim 1 wherein the probe beam illuminates a target area in the reactor fluid stream that is about 20 to 25 sq. mm.

7. The method of claim 1 wherein the laser diode light source comprises a plurality of laser bars wherein each laser bar comprises one or more laser diodes and wherein the laser bars each emit a laser beam that is multiplexed to form the pulsed laser probe beam.

8. The method of claim 7 wherein each laser bar emits light of a different wavelength.

9. The method of claim 3 wherein the laser diode light source generates a pulsed laser probe beam without employing a polarizer filter.

10. The method of claim 3 wherein the probe beam is reflected from a target area in the reactor fluid stream to form the output beam.

11. The method of claim 3 wherein the probe beam is transmitted through a target area in the reactor fluid stream to form the output beam.

12. The method of claim 3 wherein the probe beam illuminates a target area in the reactor fluid stream that is about 20 to 25 sq. mm.

13. The method of claim 3 wherein the laser diode light source comprises a plurality of laser bars wherein each laser bar comprises one or more laser diodes and wherein the laser bars each emit a laser beam that is multiplexed to form the pulsed laser probe beam and wherein each laser bar emits light of a different wavelength.

14. A method of converting a heavy hydrocarbon feed into light hydrocarbon products comprising the steps of:
    (a) mixing a heavy hydrocarbons liquid feed with catalyst particles to form a slurry;
    (b) hydrocracking heavy hydrocarbons in the slurry in the presence of hydrogen in a reactor to produce a hydrocracked slurry product comprising lighter hydrocarbon products wherein the slurry product is withdrawn from the reactor;

(c) monitoring mesophase particles in the reactor by (i) directing a pulsed laser probe beam from a laser diode light source along a first beam path into a target area in a continuous reactor fluid stream, wherein the target area is about 20 to 25 sq. mm, and wherein the probe beam comprises linearly polarized light or circularly polarized light such that an output beam emerges from the continuous reactor fluid stream along a second beam path, (ii) obtaining an image of the mesophase particles in the continuous reactor fluid stream, and (iii) analyzing the image to determine at least one of volume fraction or size distribution of mesophase particles in the continuous reactor fluid stream; and (d) adjusting reactor conditions to reduce levels of mesophae particles formed during hydrocracking.

15. The method of claim 14 wherein the laser diode light source generates a pulsed laser probe beam without employing a polarizer filter.

16. The method of claim 14 wherein the laser diode light source comprises a plurality of laser bars wherein each laser bar comprises one or more laser diodes and wherein the laser bars each emit a laser beam that is multiplexed to form the pulsed laser probe beam.

17. The method of claim 16 wherein each laser bar emits light of a different wavelength.

18. A method of converting a heavy hydrocarbon feed into light hydrocarbon products comprising the steps of:
(a) mixing a heavy hydrocarbons liquid feed with catalyst particles to form a slurry;
(b) hydrocracking heavy hydrocarbons in the slurry in the presence of hydrogen in a reactor to produce a hydrocracked slurry product comprising lighter hydrocarbon products wherein the slurry product is withdrawn from the reactor;
(c) monitoring mesophase particles in the reactor by (i) directing a pulsed laser probe beam from a laser diode light source along a first beam path into a continuous reactor fluid stream wherein the probe beam comprises linearly polarized light or circularly polarized light such that an output beam emerges from the continuous reactor fluid stream along a second beam path, wherein the laser diode light source comprises a plurality of laser bars wherein each laser bar comprises one or more laser diodes and wherein the laser bars each emit a laser beam that is multiplexed to form the pulsed laser probe beam and wherein each laser bar emits light of a different wavelength (ii) obtaining an image of the mesophase particles in the continuous reactor fluid stream, and (iii) analyzing the image to determine at least one of volume fraction or size distribution of mesophase particles in the continuous reactor fluid stream; and
(d) adjusting reactor conditions to reduce levels of mesophae particles formed during hydrocracking.

19. The method of claim 18 wherein the laser diode light source generates a pulsed laser probe beam without employing a polarizer filter.

20. The method of claim 18 wherein the probe beam illuminates a target area in the reactor fluid stream that is about 20 to 25 sq. mm.

* * * * *